(12) United States Patent
Nosrati et al.

(10) Patent No.: US 9,518,946 B2
(45) Date of Patent: Dec. 13, 2016

(54) THERMOGRAPHIC INSPECTION SYSTEM

(71) Applicant: Watlow Electric Manufacturing Company, St. Louis, MO (US)

(72) Inventors: Mohammad Nosrati, Redwood City, CA (US); Cal Swanson, St. Louis, MO (US); Kevin Ptasienski, O'Fallon, MO (US); Kevin R. Smith, Columbia, MO (US); Louis P. Steinhauser, St. Louis, MO (US)

(73) Assignee: WATLOW ELECTRIC MANUFACTURING COMPANY, St. Louis, MO (US)

( * ) Notice: Subject to any disclaimer, the term of this patent is extended or adjusted under 35 U.S.C. 154(b) by 421 days.

(21) Appl. No.: 14/097,143

(22) Filed: Dec. 4, 2013

(65) Prior Publication Data
US 2015/0153293 A1 Jun. 4, 2015

(51) Int. Cl.
*G01N 25/72* (2006.01)
*G01J 5/00* (2006.01)
*G01N 25/18* (2006.01)

(52) U.S. Cl.
CPC ............. *G01N 25/72* (2013.01); *G01N 25/18* (2013.01)

(58) Field of Classification Search
USPC ............................................. 374/5, 121, 124
See application file for complete search history.

(56) References Cited

U.S. PATENT DOCUMENTS

| | | |
|---|---|---|
| 3,752,956 A | 8/1973 | Cahill et al. |
| 6,392,205 B1 | 5/2002 | Minonishi |
| 2002/0167987 A1* | 11/2002 | Schlagheck ............ G01N 25/72 374/5 |
| 2003/0066826 A1 | 4/2003 | Lee et al. |
| 2003/0230717 A1 | 12/2003 | Reilly |
| 2004/0232136 A1 | 11/2004 | Hisaii |
| 2005/0145617 A1 | 7/2005 | McMillin et al. |
| 2006/0144516 A1 | 7/2006 | Ricci et al. |
| 2006/0274812 A1* | 12/2006 | Safai ........................ G01N 25/72 374/5 |
| 2006/0289447 A1 | 12/2006 | Mohamed et al. |
| 2007/0299628 A1* | 12/2007 | Sun ......................... G01B 21/085 702/170 |
| 2008/0011737 A1 | 1/2008 | Fukuoka et al. |
| 2009/0059461 A1 | 3/2009 | Yonekura et al. |
| 2011/0000426 A1 | 1/2011 | Herchen |

(Continued)

FOREIGN PATENT DOCUMENTS

| | | |
|---|---|---|
| EP | 1303168 | 4/2003 |
| EP | 2203028 | 6/2010 |
| WO | 03/069324 | 8/2003 |
| WO | 2007/136264 | 11/2007 |
| WO | 2010061740 | 6/2010 |

OTHER PUBLICATIONS

International Search Report for PCT/US2012/053054; (Nov. 27, 2012).

(Continued)

*Primary Examiner* — Mirellys Jagan
(74) *Attorney, Agent, or Firm* — Burris Law, PLLC

(57) ABSTRACT

A thermographic inspection system includes a heat source configured to be removably attached to an exterior surface of an object. A thermal imaging device obtains a thermal image of the object, and an analyzing device determines a location of a defect in the object based on the thermal image.

20 Claims, 4 Drawing Sheets

(56) References Cited

U.S. PATENT DOCUMENTS

| | | | |
|---|---|---|---|
| 2011/0092072 A1 | 4/2011 | Singh | |
| 2011/0142091 A1* | 6/2011 | Wardle | B82Y 15/00 374/45 |
| 2011/0249700 A1* | 10/2011 | Nakagawa | G01N 25/72 374/4 |
| 2014/0033799 A1* | 2/2014 | Newman | G01B 9/02 73/37 |

OTHER PUBLICATIONS

International Search Report for PCT/US2012/053137; (Dec. 4, 2012).
International Search Report for PCT/US2012/053148; (Jan. 8, 2013).
International Search Report for PCT/US2012/053058; (Nov. 28, 2012).
International Search Report for PCT/US2012/053069; (Nov. 27, 2012).
International Search Report for PCT/US2012/053067; (Nov. 27, 2012).
International Search Report PCT/US2012/053117 (Dec. 7, 2012).
International Search Report PCT/US2012/053049 (Nov. 28, 2012).
International Search Report for PCT/US2014/068275 dated Feb. 18, 2015.
URL:HTTP://www.watlow.com/downlaods/en/specsheets/colply0411.pdf; Polymide Heaters (Dec. 2011); pp. 1-3.
URL:http:/www.chromalox.co.uk/documents/catalog/heating_mats_for_aircraft_infrared_thermography.pdf; Chromalox: Aircraft Infrared Thermography Heating Mats; (Jun. 2009); p. 1.

* cited by examiner

THERMOGRAPHIC INSPECTION SYSTEM

FIELD

The present disclosure relates to nondestructive testing (NDT), and more particularly to thermographic inspection systems and methods for inspecting an object.

BACKGROUND

The statements in this section merely provide background information related to the present disclosure and may not constitute prior art.

Nondestructive testing (NDT) generally involves introducing an external excitation into an object to examine the object without permanently altering the material properties of the object. Thermography is one nondestructive testing technique and uses an external source of energy to heat the object and induce a temperature difference between defective and non-defective areas in the object. One common thermographic testing technique uses optical excitation where a pulsed light from a flash lamp such as a xenon flash lamp is transmitted to the object. Upon reaching an exterior surface of the object, the light is transformed into heat, which, in turn, propagates into interior of the object in the form of a thermal wave. The propagation of the thermal wave will be impeded and reflected back to the exterior surface of the object when the thermal wave hits a defect or a void in the object. The reflected thermal wave causes a local heat rise on the exterior surface. An infrared camera may be used to capture the thermal image, and namely the thermal pattern on the exterior surface. By analyzing the temperature differences on the exterior surface, the location of the defects or voids can be determined.

The typical thermography by optical excitation has its limitations. The ability of the flash lamp to introduce a thermal wave into the interior of the object is highly dependent on the optical properties of the object to be examined. An object with high reflectivity and low transmissivity can easily reflect the pulsed light away from the exterior surface of the object and allow less heat to be transformed and enter the object. As a result, the heat entering the object may not be sufficient to cause a surface temperature difference in an acceptable range to be easily visible with a thermal imaging camera.

Moreover, thermography by optical excitation is easily affected by environmental reflections and surface geometry and cannot be used for an object that has a complex shape and curvature.

SUMMARY

In one form of the present disclosure, a thermographic inspection system is provided that includes a heat source, a thermal imaging device, and an analyzing device. The heat source is configured to be removably attached to an exterior surface of an object. The thermal imaging device obtains a thermal image of the object. The analyzing device determines a location of a defect in the object based on the thermal image.

In another form of the present disclosure, a method of inspecting an object includes: removably attaching a heat source to an exterior surface of an object; energizing the heat source to generate heat; transmitting the heat to the exterior surface of the object by thermal conduction; acquiring a thermal image of the exterior surface; and determining a location of a defect in the object based on the thermal image.

In still another form, a method of inspecting an object includes: injecting heat into the object through an exterior surface of the object by thermal conduction; acquiring a thermal image of the exterior surface; and determining a location of a defect in the object based on the thermal image.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
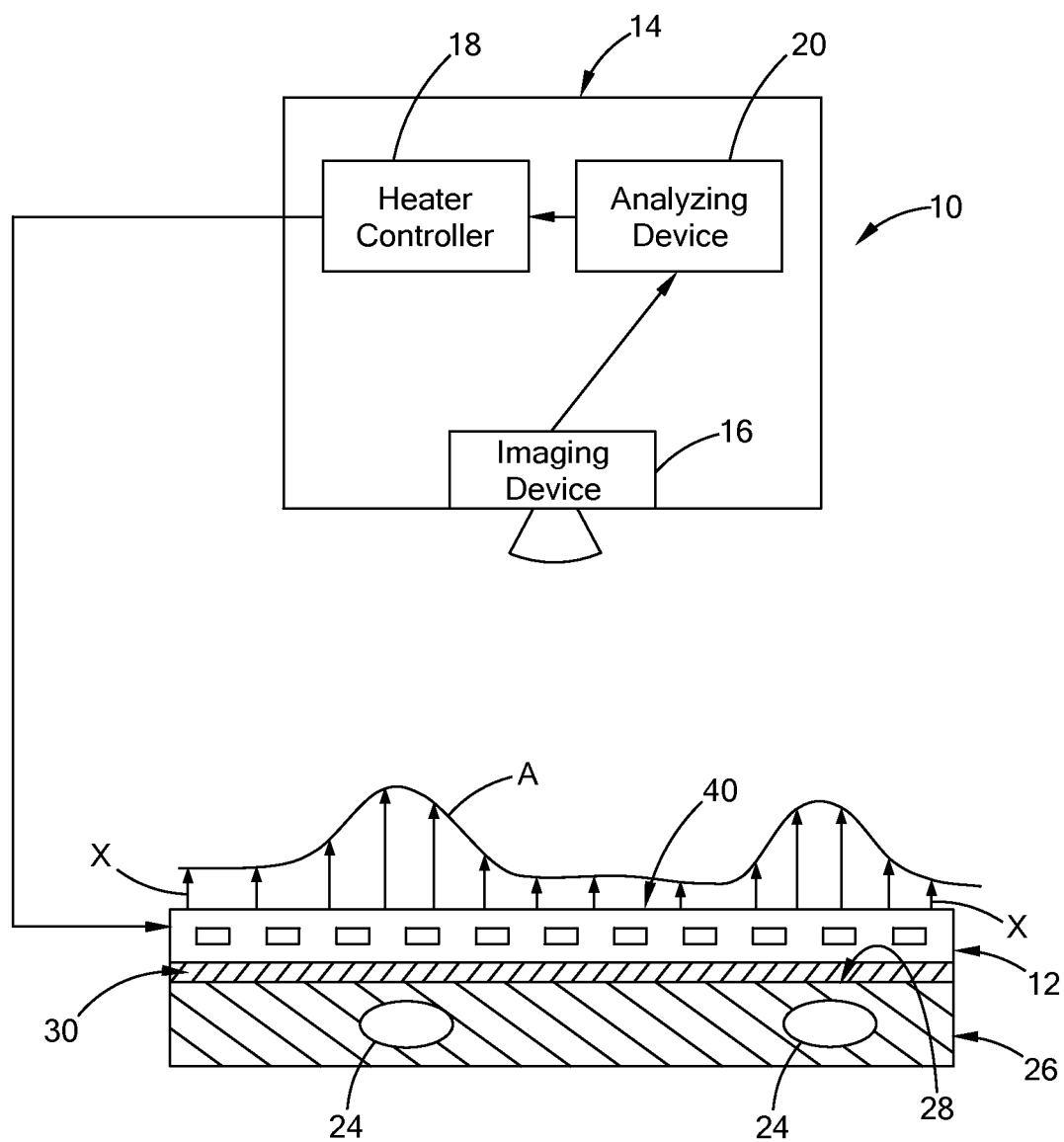
FIG. 1 is a schematic view of a thermographic inspection system constructed in accordance with the teachings of the present disclosure.

Referring to FIG. 1, a thermographic inspection system 10 in accordance with the teachings of the present disclosure includes a pixel heater 12 and a control system 14. The control system 14 includes a heater controller 16 for controlling the pixel heater 12, an imaging device 18 that acquires thermal images of the pixel heater 12, and an analyzing device 20 that determines locations of internal structures, such as defects or voids 24 in an object 26. The pixel heater 12 is formed in a sheet configuration and is removably attached to an exterior surface 28 of the object 26. The term "sheet" is defined herein as a broad, generally flat, piece of material. The sheet configuration may thus have many overall shapes such as rectangular, square, circular, triangular and the like, or may be custom shaped to fit a specific object 26. Preferably, the sheet configuration of the heater 12 is flexible to adapt to the contour(s) of the object 26 being analyzed. Likewise, the sheet configuration may itself include contours for specific applications, i.e. contours corresponding generally to the object 26, much like a sheet of material is contoured and shaped into clothing to fit the shape(s) of humans.

The pixel heater 12 may further include a self-adhesive film 30 that facilitates attachment/removal of the pixel heater 12 to/from the exterior surface 28 of the object 26. As such, the pixel heater 12 is in direct contact with the exterior surface 28 of the object 26. Alternatively, the pixel heater 12 may be disposed on the object 26 with one or more material layers (not shown) disposed between the pixel heater 12 and the exterior surface 28 of the object 26 without departing from the scope of the present disclosure as along as the heat from the pixel heater 12 can be transmitted to the object 26 by thermal conduction, and the thermal image of the object 26 can be captured by the imaging device 18. For example, the adhesive film 30 need not be integrally formed with the pixel heater 12, but may be separately formed and provided for use in attaching the heater 12 to the object 26. Likewise, in some applications an adhesive may not be required and the pixel heater 12 can be laid directly on the exterior of the object 26.

Referring to FIG. 1, while the exterior surface 28 of the object 26 is shown to be a planar surface, the pixel heater 12, due to its sheet configuration and flexibility, can be easily adapted to an object having a non-planar surface or a complex shape or curvature.

Figure 2:
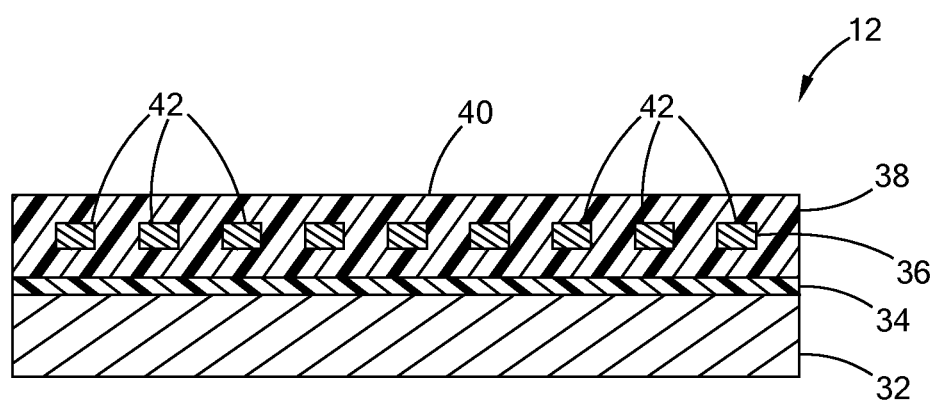
FIG. 2 is a cross-sectional view of a pixel heater of a thermographic inspection system constructed in accordance with the teachings of the present disclosure.
Figure 3:
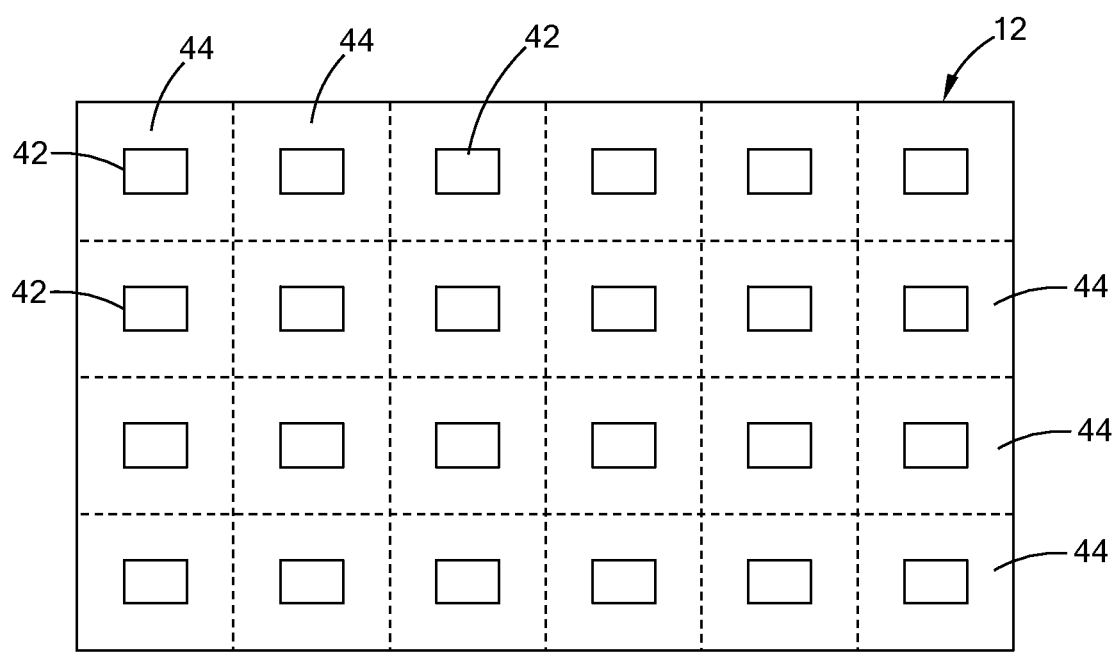
FIG. 3 is a plan view of a pixel heater of a thermographic inspection system constructed in accordance with the teachings of the present disclosure.

Referring to FIGS. 2 and 3, the pixel heater 12 includes a substrate 32, a dielectric layer 34 disposed on the substrate 32, a resistive heating layer 36 disposed on the dielectric layer 34, and a protective layer 38 disposed on and encapsulating the resistive heating layer 34. The pixel heater 12 has an exterior surface 40, which is the upper surface of the protective layer 38. The resistive heating layer 36 includes a plurality of resistive heating elements 42, which are independently controllable by the heater controller 16 and which are disposed in a plurality of heating zones 44 arranged in an array (FIG. 3). The plurality of resistive heating elements 42 are arranged along the exterior surface 28 of the object 26 and are disposed proximate the exterior surface 28 of the object 26. Therefore, the heat energy from the plurality of resistive heating elements 42 can be more precisely delivered to an area of interest in the object 26 by thermal conduction and is not affected by the reflectivity and transmissivity of the object 26. Each of the resistive heating elements 42 set forth herein are controlled by a control system. The control system may be in various forms, some of which are set forth in greater detail in pending U.S. patent application Ser. No. 13/598,939 titled "System and Method for Controlling a Thermal Array," and U.S. patent application Ser. No. 13/598,977 titled "Thermal Array System," and both are commonly assigned with the present application and the disclosures of which are incorporated herein by reference in their entirety. Generally, the control systems have a plurality of sets of power lines in communication with the resistive heating elements 42 and a plurality of addressable control elements in electrical communication with the power lines and the resistive heating elements 42, providing selective control of the pixel heater 12.

The pixel heater 12 may be a layered heater where the plurality of functional layers, including the dielectric layer 34, the resistive heating layer 36, and the protective layer 38 are formed by layered processes, such as thick film, thin film, thermal spray, and sol-gel. While shown as small squares or 'pixels', the resistive heating elements 42 may also take the form of elongated strips, concentric circles and the like. Alternatively, the pixel heater 12 may be a polyimide heater. The pixel heater 12 may be electrically connected to a power supply (not shown) by various forms, including those described in U.S. application Ser. No. 13/599,648, titled "High Definition Heater and Method of Operation," and is commonly assigned with the present application and the contents of which are incorporated herein by reference in their entirety.

Referring back to FIG. 1, the heater controller 16 of the thermographic inspection system 10 can activate the plurality of the resistive heating elements 42 of the pixel heater 12 to generate heat, which, in turn, propagates toward the object 26 in the form of thermal waves. As the thermal waves propagate toward the interior of the object 26 and hit the defects 24, the thermal waves are reflected by the defects 24 and travel toward the exterior surface 40 of the pixel heater 12. Arrows X indicate the thermal intensity on the exterior surface 40 of the pixel heater 12 at a plurality of locations. Line A shows the thermal energy distribution along the exterior surface 40 of the pixel heater 12. As shown, the thermal energy is higher at locations where defects 24 exist due to the addition of the reflected thermal waves.

The imaging device 18, which may be an infrared camera, captures thermal images of the exterior surface 40 of the pixel heater 12. It is known that all objects emit infrared radiation based on their temperatures and that the amount of radiation emitted by an object increases with temperature. Therefore, the infrared camera can capture variations in temperature on the exterior surface 40 of the pixel heater 12 by recording thermal images of the exterior surface 40 of the pixel heater 12.

The thermal images are continuously recorded as soon as the heater controller 16 activates the resistive heating elements 42. The thermal images each include a plurality of pixels corresponding to the plurality of heating zones 44. The plurality of pixels on the thermal image each have a color representing the temperature of the exterior surface 40 of the pixel heater 12. When the color of one or more pixels significantly deviate from the color of adjacent pixels, it can be determined that the specific heating zone(s) 44 that correspond(s) to this or these pixels have a higher or lower temperature than the remaining areas. Therefore, it can be determined that defects are present in the object 26 underneath the specific heating zone(s) 44.

The images captured by the imaging device 18 are sent to the analyzing device 20 to analyze the thermal image, calculate the surface temperature, and determine the locations of the defects. The analyzing device 20 may calculate the surface temperature by using the following equation:

$$Tsurf(t) - Tsurf(0) = \frac{Q}{k\rho c \sqrt{\pi t}}$$

where Tsurf(t) is the surface temperature at time t;
Tsurf(0) is the surface temperature at time 0;
Q is input heat energy per unit area;
k is thermal conductivity;
ρ is density; and
c is heat capacity.

Therefore, the analyzing device 20 determines the surface temperature of the pixel heater 12 and determines whether a specific heating zone has a higher temperature than the other heating zones 44. The analyzing device 20 then identifies the specific heating zone that has a higher temperature and the location of the defect.

Figure 4:
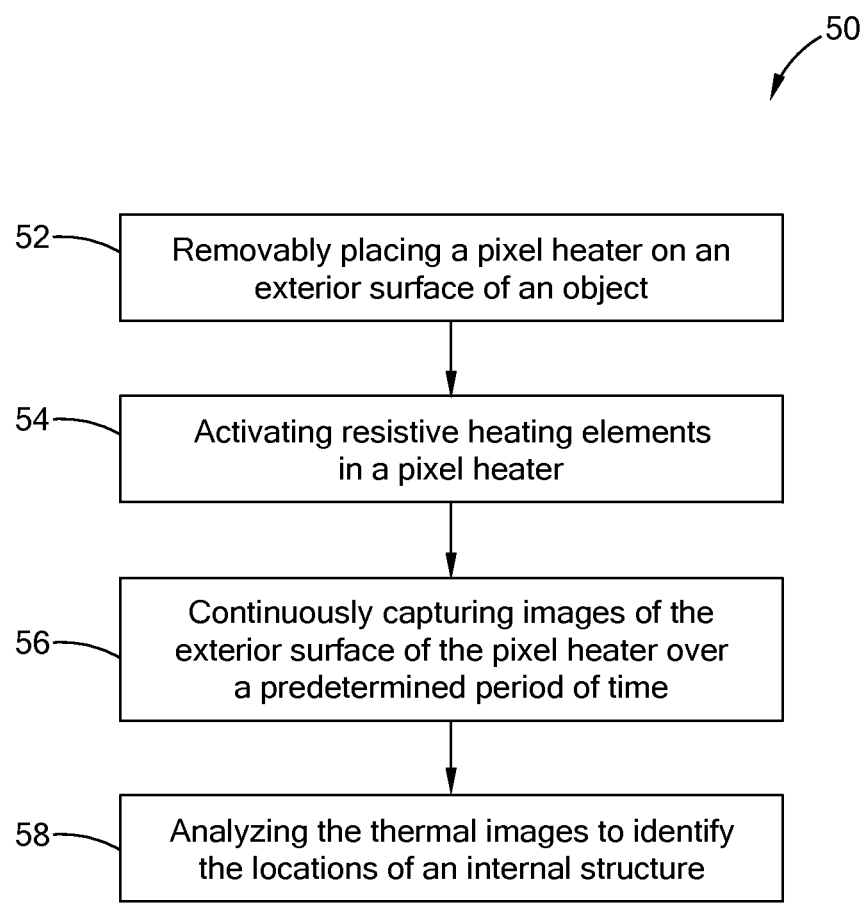
FIG. 4 is a flow diagram of a method of inspecting an object in accordance with the teachings of the present disclosure.

Referring to FIG. 4, a method 50 of inspecting an object starts with removably attaching a pixel heater 12 on an exterior surface 28 of an object 26 in step 52. The plurality of resistive heating elements 42 may be activated to generate heat in step 54. The plurality of resistive heating elements 42 may be activated simultaneously or separately depending on applications. As soon as the resistive heating elements 42 are activated, the imaging device 18 starts to record thermal images and continuously record the thermal images on the exterior surface 40 of the pixel heater 12 over a predetermined period of time in step 56. The thermal images are sent to an analyzing device 20 for analyzing the thermal pattern or temperature differences on the exterior surface 40 of the pixel heater 12 in step 58. The analyzing device 20 then determines which heating zones 44 have higher temperature than the other heating zones 44 and where internal structures, such as defects or voids 24, are based on the thermal images.

The thermographic inspection system of the present disclosure has the advantages of allowing higher heat propagation into the object due to direct thermal conduction from the heat source to the exterior surface 28 of the object 26. Because the resistive heating elements 42 are disposed proximate the object 26 to be examined, the heat can be more quickly directed to an area of interest. Because the pixel heater 12 transmits heat to the object 26 by thermal conduction, the thermographic inspection system 10 of the present disclosure can be used in a non-atmospheric environment such as vacuum and plasma, as opposed to a flash lamp where the transmitting medium (such as air) between the source of excitation and the object to be examined affects the transmission of light and the heat transformed therefrom.

Moreover, in the thermographic inspection system according to the present disclosure, because the pixel heater 12 has a plurality of resistive heating elements 42 that are independently controllable, the heat excitation of a particular area can be applied under different time-dependent analysis or cycles depending on the application. The amount of heat injected into the object 26 can be easily controlled by controlling the power to the resistive heating elements 42 and the energizing time.

Further, the thermographic inspection system according to the present disclosure can be used to inspect an object having a complex shape and curvature because the pixel heater 12 has a sheet configuration and can be easily disposed on any object. The pixel heater 12 has a relatively small footprint and thus can be used in an environment where space is limited.

It should be noted that the disclosure is not limited to the embodiments described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

What is claimed is:

1. A thermographic inspection system comprising:
   a heat source configured to be removably attached to an exterior surface of an object;
   a thermal imaging device that obtains a thermal image of the heat source; and
   an analyzing device that determines a location of a defect in the object based on the thermal image,
   wherein the heat source is disposed between the object and the thermal imaging device, and
   wherein the analyzing device determines a surface temperature of the heat source to determine the location of the defect in the object when the heat source is attached to the object.

2. The thermographic inspection system according to claim 1, wherein the heat source is a heater having a sheet configuration.

3. The thermographic inspection system according to claim 1, wherein the heat source generates heat and the heat is transmitted to the exterior surface of the object by thermal conduction.

4. The thermographic inspection system according to claim 1, wherein the heat source is in direct contact with the exterior surface of the object.

5. The thermographic inspection system according to claim 1, wherein the heat source further comprises an adhesive film connecting the heater to the exterior surface.

6. The thermographic inspection system according to claim 1, wherein the plurality of heating elements are energized differently to provide different heat energy.

7. The thermographic inspection system according to claim 1, wherein the plurality of heating elements are energized simultaneously.

8. The thermographic inspection system according to claim 1, wherein the heat source includes a polyimide heater.

9. The thermographic inspection system according to claim 1, wherein the analyzing device determines the location of the defect based on a temperature rise on the exterior surface.

10. The thermographic inspection system according to claim 1, wherein the heat source includes a plurality of heating elements that are independently controllable.

11. The thermographic inspection system according to claim 10, wherein the plurality of heating elements are disposed along the exterior surface of the object.

12. The thermographic inspection system according to claim 1, wherein the thermal imaging device includes an infrared camera.

13. The thermographic inspection system according to claim 12, wherein the infrared camera continuously acquires a plurality of thermal images over a predetermined period of time.

14. A method of inspecting an object, comprising:
    removably attaching a heat source to an exterior surface of an object;
    energizing the heat source to generate heat;
    transmitting the heat to the exterior surface of the object by thermal conduction;
    acquiring a thermal image of an exterior surface of the heat source when the heat source is attached to the exterior surface of the object; and
    determining a location of a defect in the object based on the thermal image.

15. The method according to claim 14, further comprising removably attaching the heat source to the exterior surface of the object using an adhesive film.

16. The method according to claim 15, wherein the heat source includes a plurality of resistive heating elements.

17. The method according to claim 16, further comprising independently controlling the plurality of resistive heating elements.

18. The method according to claim 16, further comprising arranging the plurality of resistive heating elements in an array and along the exterior surface of the object.

19. The method according to claim 16, further comprising analyzing the temperatures of the exterior surface at a plurality of locations corresponding to the plurality of resistive heating elements to determine the location of the defect.

20. A method of inspecting an object comprising:
    removably attaching a heat source to an exterior surface of an object;
    injecting heat into the object from the heat source through the exterior surface of the object by thermal conduction;
    acquiring a thermal image of an exterior surface of the heat source when the heat source is attached to the exterior surface of the object; and
    determining a location of a defect in the object based on the thermal image.

* * * * *